(12) United States Patent
Seo et al.

(10) Patent No.: US 12,722,019 B2
(45) Date of Patent: Sep. 1, 2026

(54) APPARATUS FOR PROVIDING STIMULATION BASED ON RADIO FREQUENCY CURRENT AND PLASMA

(71) Applicants: Suk Bae Seo, Seoul (KR); Ho Joon Seo, Seoul (KR); Ja Young Kim, Seoul (KR)

(72) Inventors: Suk Bae Seo, Seoul (KR); Ho Joon Seo, Seoul (KR); Ja Young Kim, Seoul (KR)

( * ) Notice: Subject to any disclaimer, the term of this patent is extended or adjusted under 35 U.S.C. 154(b) by 372 days.

(21) Appl. No.: 18/508,026

(22) Filed: Nov. 13, 2023

(65) Prior Publication Data

US 2024/0198120 A1 Jun. 20, 2024

Related U.S. Application Data

(63) Continuation of application No. PCT/KR2022/006886, filed on May 13, 2022.

(30) Foreign Application Priority Data

May 13, 2021 (KR) ........................ 10-2021-0061769
May 13, 2022 (KR) ........................ 10-2022-0058701

(51) Int. Cl.
*A61N 1/40* (2006.01)
*A61N 1/04* (2006.01)
(Continued)

(52) U.S. Cl.
CPC ........... *A61N 1/403* (2013.01); *A61N 1/0502* (2013.01); *A61N 1/36017* (2013.01);
(Continued)

(58) Field of Classification Search
CPC .. A61N 1/403; A61N 1/0502; A61N 1/36017; A61N 1/36034; A61N 1/0472;
(Continued)

(56) References Cited

U.S. PATENT DOCUMENTS 9,364,392 B2 6/2016 Ko
9,744,371 B2 8/2017 Ko
(Continued)

FOREIGN PATENT DOCUMENTS

JP 2013-211153 A 10/2013
KR 10-2006-0012067 A 2/2006
(Continued)

OTHER PUBLICATIONS

Office Action issued in KR 10-2022-0058701; mailed by the Korean Intellectual Property Office on Jan. 20, 2023.
(Continued)

*Primary Examiner* — Beverly M Flanagan
(74) *Attorney, Agent, or Firm* — Studebaker Brackett PLLC

(57) ABSTRACT

A stimulation providing apparatus, based on an RF current and plasma, is disclosed. The apparatus includes a housing inserted into skin, a hollow tube formed inside and along a lengthwise direction of the housing, an injection hole formed at one end of the hollow tube, and into which gas is injected, a first current providing part, formed at a distal end of an inner surface of the hollow tube and providing a first current to inside the hollow tube, a second current providing part, formed at a distal end of an outer surface of the housing and providing a second current to the skin, a controller that controls the first and current providing parts to sequentially providing the first and second currents, and at least one discharge hole, formed at an opposite end of the hollow tube and discharging plasma generated at a distal end of the hollow tube.

14 Claims, 9 Drawing Sheets

(51) Int. Cl.
*A61N 1/05* (2006.01)
*A61N 1/36* (2006.01)
*A61N 1/44* (2006.01)

(52) U.S. Cl.
CPC .......... *A61N 1/36034* (2017.08); *A61N 1/44* (2013.01); *A61N 1/0472* (2013.01)

(58) Field of Classification Search
CPC ... A61N 1/44; A61N 1/05; A61N 1/06; A61N 1/08; A61N 1/32; A61N 1/36; A61N 1/328; H05H 1/24; A61M 35/00
USPC .......................................................... 607/101
See application file for complete search history.

(56) References Cited

U.S. PATENT DOCUMENTS 10,035,024 B2 7/2018 Ko
10,342,985 B2 7/2019 Ko
10,820,937 B2 11/2020 Hancock et al.
11,071,873 B2 7/2021 Ko
2014/0194789 A1 7/2014 Ko
2015/0214013 A1* 7/2015 Glukhoy .......... H01J 37/32477 29/527.1
2016/0271410 A1 9/2016 Ko
2017/0326376 A1 11/2017 Ko
2018/0304089 A1 10/2018 Ko
2019/0083159 A1 3/2019 Hancock et al.
2019/0290926 A1 9/2019 Ko

FOREIGN PATENT DOCUMENTS

KR 10-0993491 B1 11/2010
KR 10-1300123 B1 8/2013
KR 10-2015-0146253 A 12/2015
KR 10-2018-0123005 A 11/2018
KR 10-1970644 B1 8/2019
KR 10-2020-0136118 A 12/2020
KR 10-2380650 B1 4/2022
WO WO-2012167089 A1 * 12/2012 .............. A61N 1/44

OTHER PUBLICATIONS

International Search Report issued in PCT/KR2022/006886; mailed Aug. 30, 2022.

* cited by examiner

FIG. 6B

APPARATUS FOR PROVIDING STIMULATION BASED ON RADIO FREQUENCY CURRENT AND PLASMA

CROSS-REFERENCE TO RELATED APPLICATIONS

The present application is a continuation of International Patent Application No. PCT/KR2022/006886 filed on May 13, 2022, which is based upon and claims the benefit of priority to Korean Patent Application Nos. 10-2021-0061769 filed on May 13, 2021 and 10-2022-0058701 filed on May 13, 2022 The disclosures of the above-listed applications are hereby incorporated by reference herein in their entirety.

BACKGROUND

Embodiments of the present disclosure described herein relate to an apparatus for providing a stimulation based on an RF current and plasma.

Plasma refers to a state, in which gas is heated to an extremely high temperature and separated into electrons and protons.

Recently, plasma has been found to be excellent for skin regeneration. Accordingly, the development of a skin care apparatus using plasma is being actively conducted.

However, according to the conventional skin care apparatus using plasma, a current for generating plasma is delivered to an outside of the apparatus that is inserted into skin, and thus, the patient who receives skin care may feel pain.

SUMMARY

Embodiments of the present disclosure provide an apparatus for providing a stimulation based on an RF current and plasma.

The technical problems to be solved by the present disclosure are not limited to the aforementioned problems, and any other technical problems not mentioned herein will be clearly understood from the following description by those skilled in the art to which the present disclosure pertains.

According to an embodiment, an apparatus for providing a stimulation based on an RF current and plasma includes a housing inserted into skin, a hollow tube formed along a lengthwise direction of the housing in an interior of the housing, an injection hole formed at one end of the hollow tube, and into which at least one gas is injected, a first current providing part formed at a distal end of an inner surface of the hollow tube, and that provides a first current to an interior of the hollow tube, a second current providing part formed at a distal end of an outer surface of the housing, and that provides a second current to the skin, a controller that controls the first current providing part and the second current providing part such that the first current and the second current are sequentially provided, and at least one discharge hole formed at an opposite end of the hollow tube, and that discharges plasma generated at a distal end of the hollow tube.

In the present disclosure, the controller may sequentially provide the plasma and the second current to the skin through switching of a first mode for providing the first current and a second mode for providing the second current.

In the present disclosure, the first current providing part may be connected to a first electrode for activating the first mode, and the second current providing part may be connected to a second electrode for activating the second mode.

In the present disclosure, in the first mode, the controller may provide the first current through the first current providing part by applying a voltage of a first intensity through the first electrode, and in the second mode, the controller may provide the second current through the second current providing part by applying a voltage of a second intensity through the second electrode.

In the present disclosure, a portion of the inner surface of the hollow tube, except for the first current providing part, may be formed in an insulated state, and a portion of the outer surface of the housing, except for the second current providing part, may be formed in an insulated state.

In the present disclosure, when sensing that the housing is inserted into the skin by a preset depth or more, the controller may control the first current providing part to provide the first current or controls the second current providing part to provide the second current.

In the present disclosure, when a plurality of discharge holes are provided, the controller may change patterns of the plurality of discharge holes through a pattern changing part.

In the present disclosure, the housing may be formed of a needle type or a cannula type.

According to an embodiment, a plurality of needle tips for providing a stimulation based on plasma includes a needle fixing part and a plurality of needles, and each of the plurality of needles includes a hollow tube formed along a lengthwise direction of the needle at a center of an interior thereof, an injection hole formed at one end of the hollow tube, and to which at least one gas is injected, a current providing part formed at a distal end of the hollow tube, and that provides a current to an interior of the hollow tube, a controller that generates plasma at the distal end of the hollow tube by controlling the current providing part to apply the current to a gas flowing through the hollow tube, and at least one discharge hole formed at an opposite end of the hollow tube, and through which the plasma generated at the distal end of the hollow tube is discharged.

According to an embodiment, a cannula fixing part and a plurality of cannulas are provided, and each of the cannulas includes a hollow tube formed along a lengthwise direction of the needle at a center of an interior thereof, an injection hole formed at one end of the hollow tube, and to which at least one gas is injected, a current providing part formed at a distal end of the hollow tube, and that provides a current to an interior of the hollow tube, a controller that generates plasma at the distal end of the hollow tube by controlling the current providing part to apply the current to a gas flowing through the hollow tube, and at least one discharge hole formed at an opposite end of the hollow tube, and through which the plasma generated at the distal end of the hollow tube is discharged.

Other detailed items of the present disclosure are included in the detailed description of the present disclosure and the drawings.

BRIEF DESCRIPTION OF THE FIGURES

The above and other objects and features will become apparent from the following description with reference to the following figures, wherein like reference numerals refer to like parts throughout the various figures unless otherwise specified, and wherein:

FIGS. 6A and 6B are views illustrating a pattern of a discharge hole according to an embodiment of the present disclosure;

DETAILED DESCRIPTION

Figure 1:
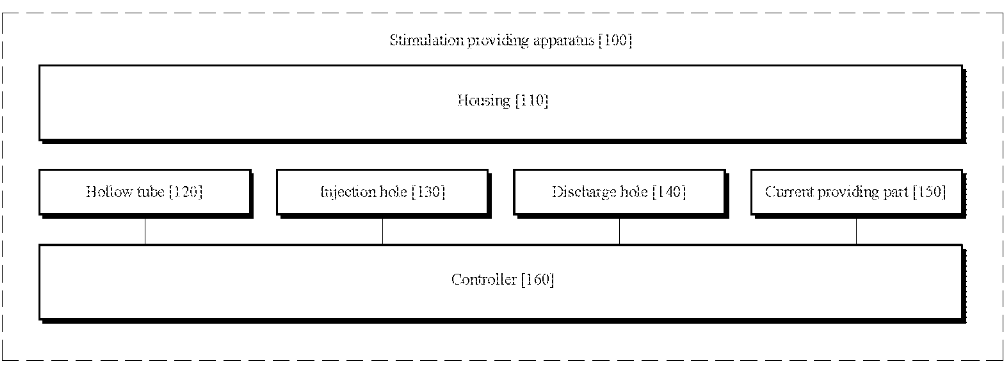
FIG. 1 is a block diagram of an apparatus for providing a stimulation based on plasma according to an embodiment of the present disclosure.

The advantages and features of the present disclosure, and a method for achieving them will become clear with reference to the embodiments that will be described in detail together with the accompanying drawings. However, the present disclosure is not limited by the embodiments disclosed hereinafter but may be implemented in various different forms, and the embodiments are provided simply to make the disclosure of the present disclosure complete and inform an ordinary person in the art of the scope of the present disclosure, and the disclosure is only defined by the scope of the claims.

The terms used in the specification is for describing the embodiments, and is not intended to limit the present disclosure. A singular expression includes a plural expression unless an exemption is particularly described in the specification. The expression "comprises" and/or "comprising" used in the specification does not exclude presence or addition of one or more other components, in addition to the mentioned components. throughout the specification, the same reference numerals denote the same components, and the term "and/or" includes one or more combinations of the mentioned components. Although "first", "second", or the like is used to describe various components, it is apparent that the components are not limited by the terns. The terms are used simply to distinguish one component from another component. Accordingly, it is apparent that a first component mentioned hereinafter may be a second component in the technical spirit of the present disclosure.

Unless otherwise defined, all terms (including technical and scientific terms) used herein have the same meaning as commonly understood by those skilled in the art, to which the present disclosure pertains. Furthermore, the terms defined in commonly used dictionaries should not be interpreted in an idealized or overly formal sense unless expressly so defined herein The spatially relative terms, such as "below", "beneath", "lower", "above" and "upper", are used to describe an associative relationship between one component and the other components as illustrated in the drawings. The spatially relative terms should be understood as terms including different directions of the components during use or an operation thereof, in addition to the directions illustrated in the drawings. For example, the components illustrated in the drawings are turned over, a component described as being "below" or "beneath" another component may be positioned "above" the second component. Accordingly, the illustrative term "beneath" or "below" may include all of the upward and downward directions. The component may be oriented in different directions, and thus, the spatially relative terms may be interpreted according to orientations.

Hereinafter, embodiments of the present disclosure will be described in detail with reference to the accompanying drawings.

FIG. 1 is a block diagram of an apparatus for providing a stimulation based on plasma according to an embodiment of the present disclosure.

Figure 2:
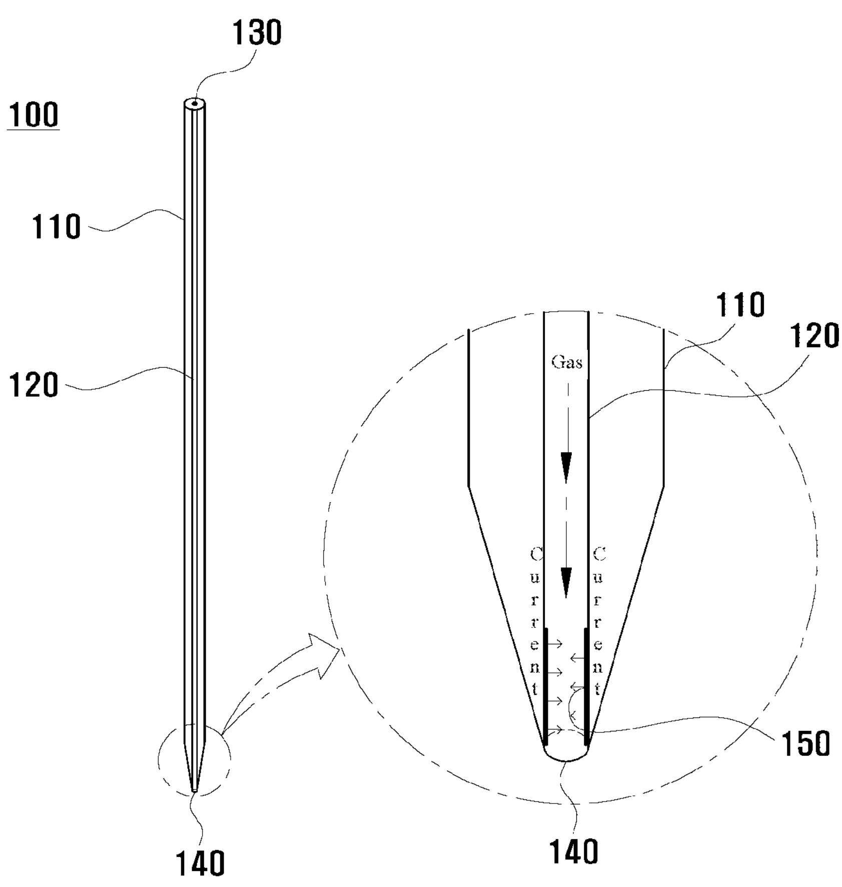
FIG. 2 is a view illustrating an apparatus for providing a stimulation based on plasma according to an embodiment of the present disclosure.

FIG. 2 is a view illustrating the apparatus for providing a stimulation based on plasma according to an embodiment of the present disclosure.

Figure 3:
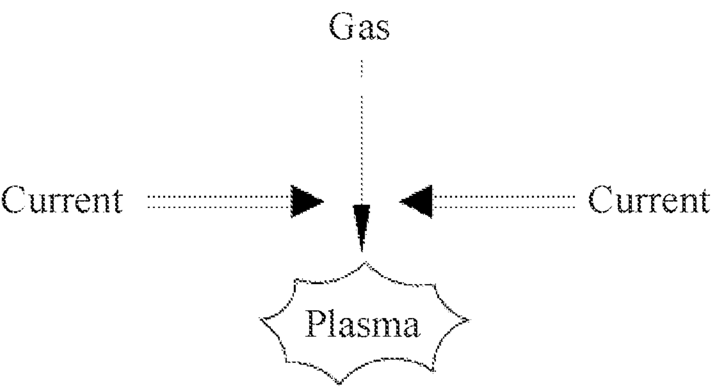
FIG. 3 is a view illustrating plasma according to an embodiment of the present disclosure.

FIG. 3 is a view illustrating plasma according to an embodiment of the present disclosure.

Figure 4:
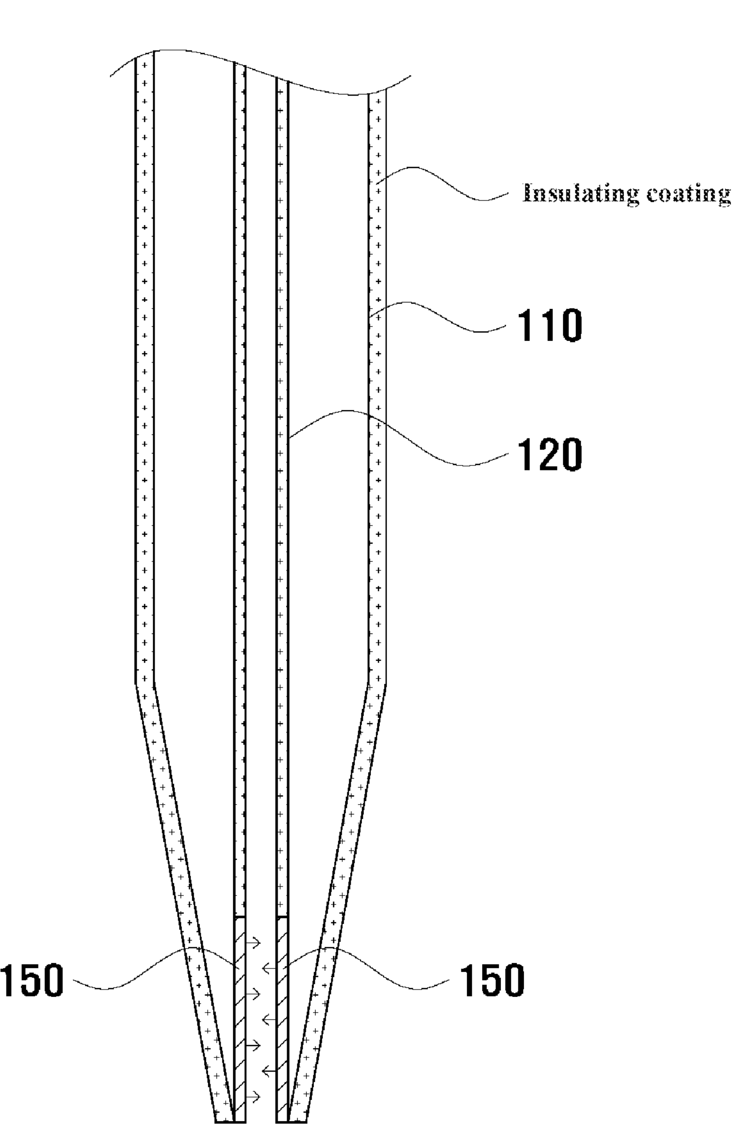
FIG. 4 is a view illustrating a housing that is formed in an insulated state according to an embodiment of the present disclosure.

FIG. 4 is a view illustrating a housing that is formed in an insulated state according to an embodiment of the present disclosure.

Figure 5:
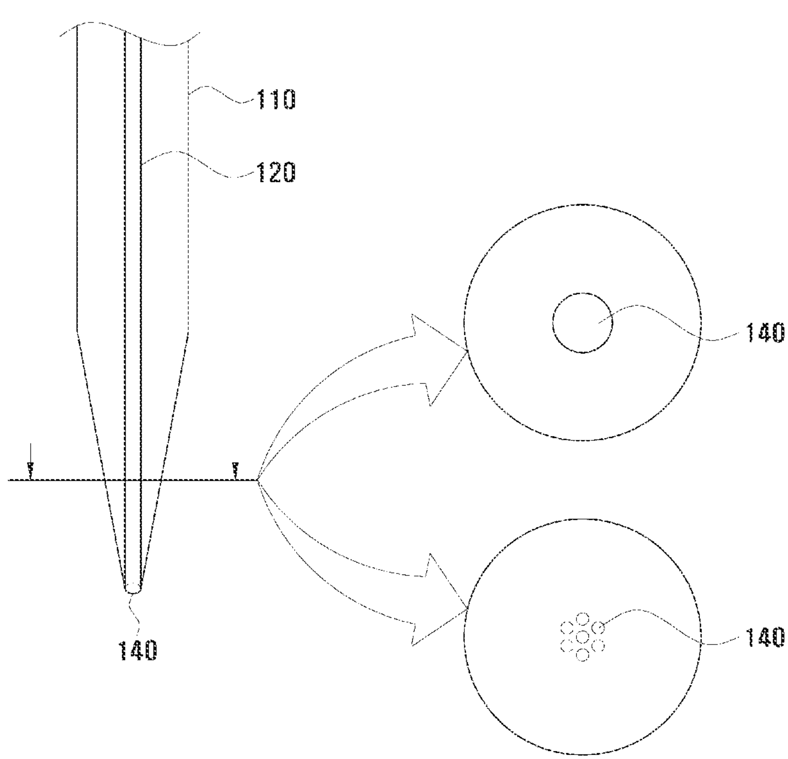
FIG. 5 is a view illustrating a discharge hole according to an embodiment of the present disclosure.

FIG. 5 is a view illustrating a discharge hole according to an embodiment of the present disclosure.

Figure 6A:
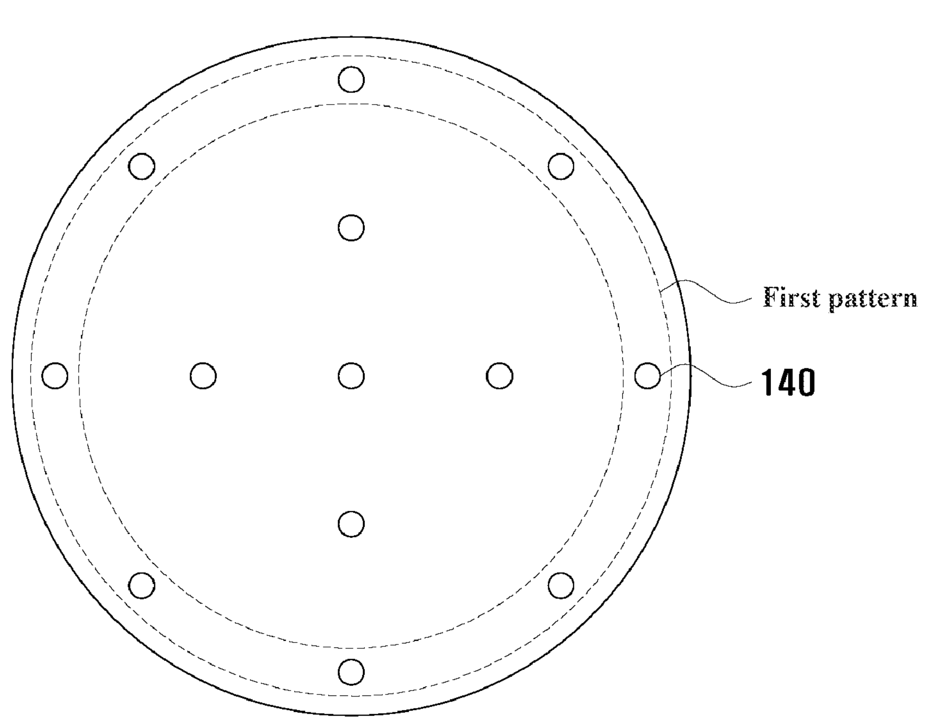
Figure 6B:
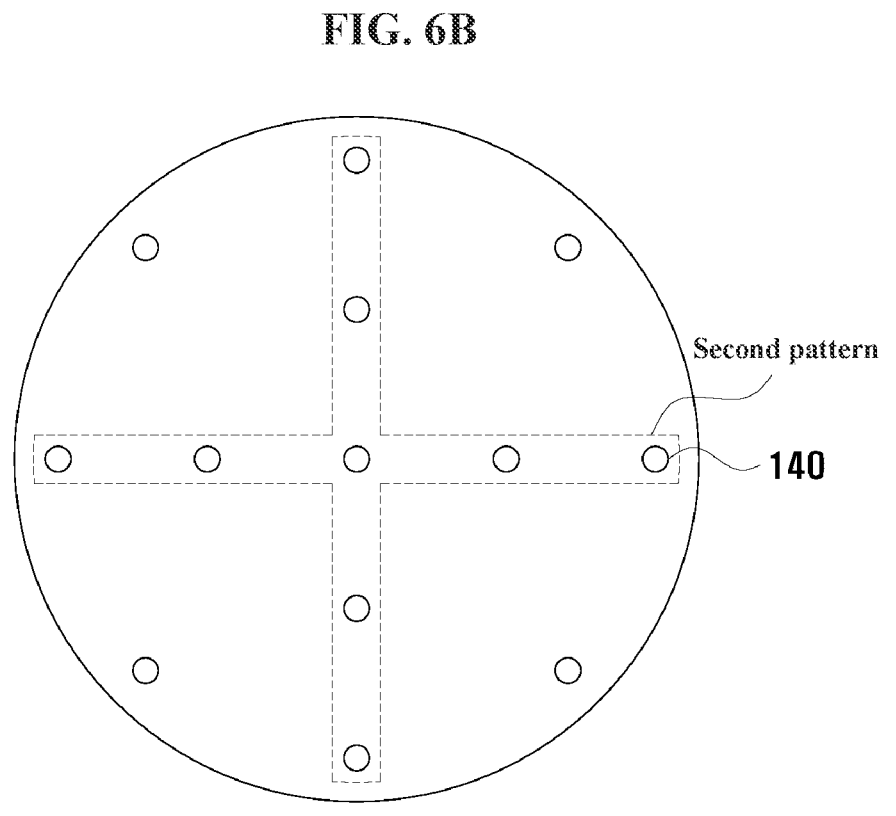

FIGS. 6A and 6B are views illustrating a pattern of the discharge hole according to an embodiment of the present disclosure.

Referring to FIG. 1, an apparatus for providing a stimulation based on plasma 100 (hereinafter referred to as stimulation providing apparatus) may include a housing 110, a hollow tube 120, an injection hole 130, a discharge hole 140, a current providing part 150, and a controller 160.

However, in some embodiments, the stimulation providing apparatus 100 may include fewer or more components than those illustrated in FIG. 1.

According to an embodiment, the stimulation providing apparatus 100 may be an apparatus that is inserted into skin of a patient to stimulate a dermal layer of the skin by using plasma so that the skin may automatically regenerate damage that is caused by a stimulus.

The housing 110 of the stimulation providing apparatus 100 may be formed to be thin and sharp as illustrated in FIG. 2 to be smoothly inserted into the skin.

More specifically, the housing 110 of the stimulation providing apparatus 100 may be formed of a needle type, or may be formed of a cannula type.

The hollow tube 120 may be formed along a longitudinal direction of the housing 110 as illustrated in FIG. 2. Then, an inner surface of the housing 110 may be an outer surface of the hollow tube 120. That is, the housing 110 itself may be formed in a hollow shape. However, the present disclosure is not limited thereto, and the hollow tube 120 may be included as a separate tube in an interior of the housing 110.

The injection hole 130 may be formed at one end of the hollow tube 120, and at least one gas may be injected therethrough. Then, the kind of the injected gas is not limited as long as it is harmless to a human body. For example, the injected gas may be carbon dioxide (CO2).

The gas injected through the injection hole 130 may flow through the hollow tube 120.

The current providing part 150 may be formed at a distal end of the hollow tube 120 and may provide a current to an interior of the hollow tube 120. Then, the current may be an alternating current. For example, the current providing part 150 may provide an RF (radio frequency) current, but the current provided by the current providing part 150 is not limited thereto. That is, the current according to the present disclosure may include all types of currents that may generate plasma while reacting with the gas flowing to the interior of the hollow tube 120.

The controller 160 may control the current providing part 150 so that the current is applied to the gas flowing through the hollow tube 120 to generate the plasma at the distal end of the hollow tube 120.

The discharge hole 140 may be formed at an opposite end of the hollow tube 120, and may cause the plasma generated at the distal end of the hollow tube 120 to be discharged.

Referring to FIG. 3, when the gas and the current contact at the distal end in the interior of the hollow tube 120, the plasma may be generated according to the contact reaction between the gas and the current. Then, an intensity and a size of the plasma may be generated differently depending on the type of the gas.

The plasma generated in this way may be discharged into the skin through at least one discharge hole 140 that is formed at the opposite end of the hollow tube 120. The plasma discharged into the skin may stimulate the dermal layer and cause skin regeneration to occur automatically inside the skin.

The controller 160 of the present disclosure is not included in the interior of the housing 110, but may be included in an individual apparatus outside the housing 110 to control components included in the interior of the housing 110.

According to an embodiment, the controller 160 may be included in a handpiece (not illustrated) that is connected to the housing 110.

More specifically, the housing 110 that is formed of a needle type or a cannula type may be connected to the handpiece (not illustrated) through at least one connection member.

The handpiece (not illustrated) is a part which a doctor grips, and the doctor may perform a control, through the controller 160 that is included in the handpiece (not illustrated), such that the housing 110 formed of the needle type or the cannula type is inserted into the skin to generate the plasma while moving the handpiece (not illustrated) on the skin of the patient.

The controller 160 may control the gas to be injected through the injection hole 130 when sensing that the housing 110 is inserted into the skin at a preset depth or more.

The controller 160 may control the current providing part 150 to provide the current when sensing that the housing 110 is inserted into the skin at the preset depth or more.

That is, when the housing 110 is inserted into the skin at the preset depth or more (for example, a depth that is large enough to reach the dermis layer), the controller 160 may inject the gas through the injection hole 130 so that the gas flows through the hollow tube 120, and may provide the current through the current providing part 150 by applying the current, and may generate the plasma when the gas and the current meet each other to react with each other at the distal end of the hollow tube 120.

Then, a driving part (not illustrated) may be included in an interior of the handpiece (not illustrated), and the controller 160 may cause the housing 110 to be inserted into the skin through the driving part (not illustrated). For example, the housing 110 may be inserted into the skin through an upward/downward movement of the driving part (not illustrated), and the housing 110 may be lowered through striking of the driving part (not illustrated) to be inserted into the skin.

An outer surface of the housing 110 of the stimulation providing apparatus 100 of the present disclosure may be formed in an insulated state. An existing skin care apparatus using an electric current directly provides a current to skin, and thus, patients may feel pain However, according to the present disclosure, by insulating the outer surface of the housing 110 through coating, the current may be prevented from passing through an outside (a skin contact area) of the housing 110, and thus, the current may be provided only through the current providing part 150 in the interior of the housing 110. Here, the insulating coating may mean processing, such as applying or attaching an insulating material to the outer surface.

According to the embodiment, some areas of an inner surface of the housing 110 of the stimulation providing apparatus 100 also may be formed in an insulated state.

Referring to FIG. 4, an entire outer surface of the housing 110 may be formed in an insulated state, and some areas of the inner surface (all areas except the distal end) may be formed in an insulated state. This means that the current applied to the interior of the apparatus 100 by the controller 160 is provided intensely only at the distal end (i.e., the distal end of the hollow tube 120) of the housing 110 in an uninsulated state. In this case, the current providing part 150 may be formed only at the distal end of the inner surface of the hollow tube 120 to provide the current only at the distal end, and the provided current may react the gas that flows through the hollow tube 120 from the distal end.

As described above, the distal end of the housing 110 in an insertion direction in the present disclosure may include at least one discharge hole 140 that causes the generated plasma to be discharged into the skin, at a lower end of the hollow tube 120 with respect to the insertion direction of the housing 110.

FIG. 5 illustrates a cross-sectional view viewed from a top while cutting the distal end of the housing 110 in the insertion direction transversely. As illustrated in FIG. 5, one discharge hole 140 or a plurality of discharge holes 140 may be provided.

When one discharge hole 140 is provided, a size of the hole may be relatively large.

When a plurality of discharge holes 140 are provided, the sizes of the holes may be formed to be relatively small because several discharge holes 140 have to be formed in an area corresponding to a size of the hole when only one discharge hole 140 is provided.

Accordingly, when only the one discharge hole 140 is provided, a stimulus may be provided over a relatively large area when the plasma is discharged into the skin, and when the plurality of discharge holes 140 are provided, a stimulus may be provided through multiple paths in a relatively small area when the plasma may be discharged into the skin.

According to an embodiment, the stimulation providing apparatus 100 may further include a hole changing part (not illustrated), and the controller 160 changes the number of discharge holes 140 through the hole changing part (not illustrated).

More specifically, the controller 160 may change the number of the discharge holes 140 depending on an area of the skin, in which the stimulation providing apparatus 100 is inserted and a skin condition of the patient. In some cases, the one discharge hole 140 may be provided at a lower end of the hollow tube 120 to provide a stimulus over a large area inside the skin, or in some cases, the plurality of discharge holes 140 may be provided at the lower end of the hollow tube 120 to provide a stimulus through multiple paths in a small area inside the skin.

According to an embodiment, the controller 160 may change the number of discharge holes 140 through the hole changing part (not illustrated) while the housing 110 is inserted into the skin and the plasma is generated.

More specifically, in a state, in which the housing 110 is inserted into the skin and the plasma is generated to provide a wide stimulus to the skin while the one discharge hole 140 is provided at the lower end of the hollow tube 120, the controller 160 may provide a fine stimulus through the plasma to the inside of the skin by changing the number of discharge hole 140 from the one discharge hole 140 to the plurality state through the hole changing part (not illustrated).

The stimulation providing apparatus 100 may further include a pattern changing part (not illustrated), and may cause the controller 160 to change the patterns of the plurality of discharge holes 140 through the pattern changing part (not illustrated).

More specifically, the pattern changing part (not illustrated) may include a plurality of plates having different patterns. As illustrated in FIG. 6A, a first plate may include a strip-shaped first pattern. As illustrated in FIG. 6B, a second plate may include a second cross-shaped pattern. The shape of the pattern is not limited thereto, and is various.

When the controller 160 changes a basic plate (in a state, in which the plurality of discharge holes 140 are fully opened) to the first plate through the pattern changing part (not illustrated), among the plurality of discharge holes 140, only the discharge hole 140 included in the first pattern is opened, and the plasma is discharged only from the corresponding discharge hole 140. That is, the plasma may be discharged into the skin in a strip shape.

When the controller 160 changes the basic plate (in which, the plurality of discharge holes 140 are fully opened) to the second plate through the pattern changing part (not illustrated), among the plurality of discharge holes 140, only the discharge hole 140 included in the second pattern is opened, and the plasma is discharged only from the corresponding discharge hole 140. That is, the plasma may be discharged into the skin in a cross shape.

When the controller 160 converts the first plate to the second plate through the pattern changing part (not illustrated), a state, in which among the plurality of discharge holes 140, only the discharge hole 140 included in the first pattern is opened, is changed to a state, in which the discharge hole 140 included in the second pattern is opened whereby the plasma is discharged only from the corresponding discharge hole 140. That is, the plasma may be discharged into the skin in a strip shape and then may be changed into a cross shape and be discharged.

As described above, the stimulation providing apparatus 100 of the present disclosure may be formed of a needle type or a cannula type.

According to an embodiment, a needle tip that provides a plasma-based stimulation may be implemented using the stimulation providing apparatus 100 formed of a needle type. That is, the stimulation providing apparatus 100 formed of a needle type may be included in the needle tip as a needle unit. Hereinafter, the needle tip that provides a plasma-based stimulation will be described.

The needle tip may include a needle fixing part and a plurality of needles that are inserted into the skin.

A plurality of needles may be inserted into and fixed to the needle fixing part.

Each of the plurality of needles may include the hollow tube 120 that is formed along a lengthwise direction of the needle at a center of an interior thereof, the injection hole 130 that is formed at one end of the hollow tube 120, and to which at least one gas is injected, the current providing part 150 that is formed at a distal end of the hollow tube 120, and that provides a current to the interior of the hollow tube 120, the controller 160 that generates the plasma at the distal end of the hollow tube 120 by controlling the current providing part 150 to apply the current to a gas that flows through the hollow tube 120, and at least one discharge hole 140 that is formed at an opposite end of the hollow tube 120, and through which the plasma generated at the distal end of the hollow tube 120 is discharged. Here, a detailed description of the hollow tube 120, the injection hole 130, the discharge hole 140, the current providing part 150, and the controller 160 are the same as those described with reference to FIGS. 1 to 6, and will be omitted.

According to an embodiment, a cannula tip that provides a plasma-based stimulation may be implemented by using the stimulation providing apparatus 100 that is formed of a cannula type. That is, the stimulation providing apparatus 100 formed of a cannula type may be included in a cannula tip as a cannula unit. Hereinafter, the cannula tip that provides a plasma-based stimulation will be described.

The cannula tip may include a cannula fixing part and a plurality of cannulas that are inserted into the skin A plurality of cannulas may be inserted into and fixed to the cannula fixing part Each of the plurality of cannulas may include the hollow tube 120 that is formed along a lengthwise direction of the cannula at a center of an interior thereof, the injection hole 130 that is formed at one end of the hollow tube and through which at least one gas is injected, the current providing part 150 that is formed at a distal end of the hollow tube 120, and that provides a current to the interior of the hollow tube 120, the controller 160 that generates the plasma at the distal end of the hollow tube 120 by controlling the current providing part 150 to apply the current to a gas that flows through the hollow tube 120, and at least one discharge hole 140 that is formed at an opposite end of the hollow tube 120, and through which the plasma generated at the distal end of the hollow tube 120 is discharged. Here, a detailed description of the hollow tube 120, the injection hole 130, the discharge hole 140, the current providing part 150, and the controller 160 are the same as those described with reference to FIGS. 1 to 6, and will be omitted.

Hereinafter, the apparatus that sequentially provides an RF current and plasma will be described with reference to FIGS. 7 and 8.

Figure 7:
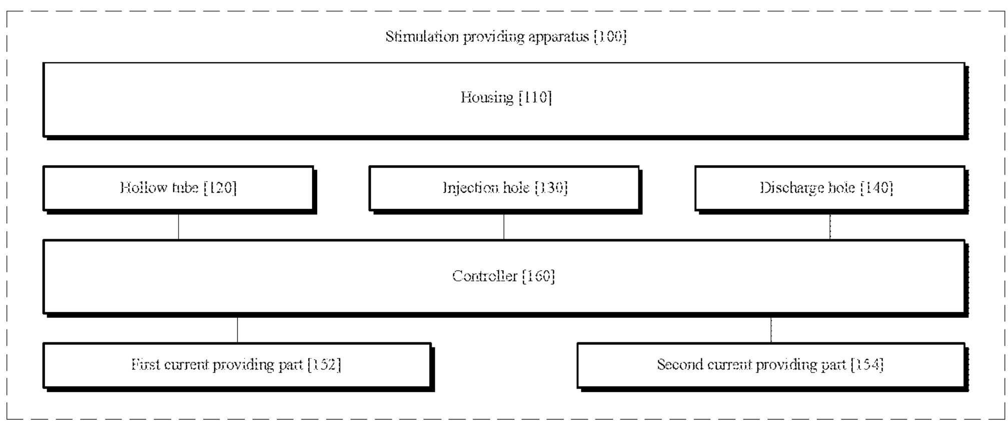
FIG. 7 is a block diagram of an apparatus for providing a stimulation based on an RF current and plasma according to another embodiment of the present disclosure.

FIG. 7 is a block diagram of an apparatus for providing a stimulation based on an RF current and plasma according to another embodiment of the present disclosure.

Figure 8:
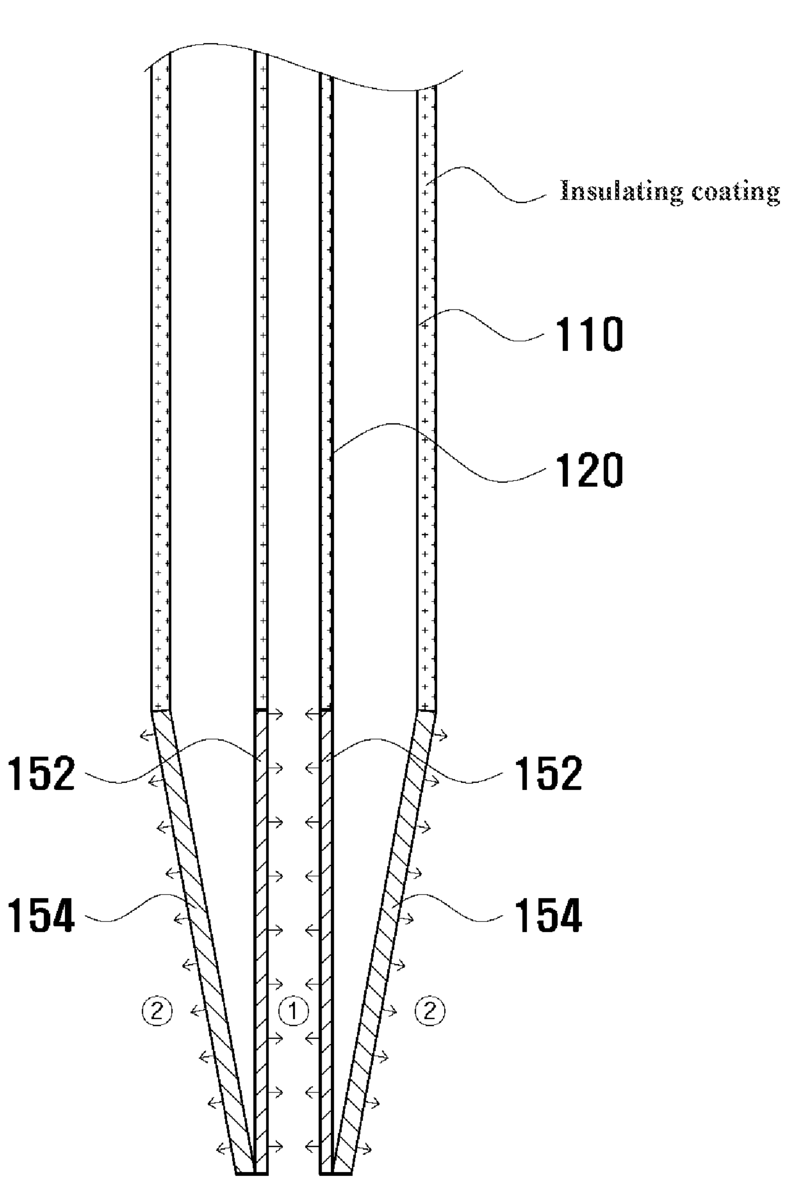
FIG. 8 is a view illustrating sequential provision of an RF current and plasma according to another embodiment of the present disclosure.

FIG. 8 is a view illustrating the sequential provision of the RF current and the plasma according to another embodiment of the present disclosure.

According to an embodiment, an apparatus for providing a stimulation based on an RF current and plasma 100 (hereinafter referred to as a stimulation providing apparatus) may be an apparatus that is inserted into skin of a patient and sequentially outputs plasma and an RF current to apply different kinds of stimuli to the dermal layer of the skin to automatically regenerate damage caused by the stimulus.

Referring to FIG. 7, the stimulation providing apparatus 100 may include the housing 110, the hollow tube 120, the injection hole 130, the discharge hole 140, a first current providing part 152, and a second current providing part 154, and the controller 160.

However, in some embodiments, the stimulation providing apparatus 100 may include fewer or more components than those illustrated in FIG. 7.

Because a description of the housing 110, the hollow tube 120, the injection hole 130, and the discharge hole 140 is repeated with those described with reference to FIGS. 1 to 6B, a detailed description thereof will be omitted.

As illustrated in FIG. 8, the first current providing part 152 may be formed at the distal end of the inner surface of the hollow tube 120 to provide the first current to the interior of the hollow tube 120. When the applied first current contacts the gas that flows through the hollow tube 120, plasma may be generated according to a contact reaction between the gas and the first current. The plasma generated in this way may be output to the outside of the apparatus 100 and may stimulate the interior of the skin.

Then, the first current may be an alternating current. The first current provided by the current providing part 150 is not limited thereto, and may include all kinds of currents that may generate plasma while reacting with the gas that flows in the interior of the hollow tube 120.

As illustrated in FIG. 8, the second current providing part 154 may be formed at the distal end of the outer surface of the housing 110, and may directly stimulate the interior of the skin by providing the second current to the skin.

As illustrated in FIG. 8, the stimulation providing apparatus 100 may be formed such that the inner surface of the hollow tube 120, except for the first current providing part 152, is in an insulated state. This means that the first current applied to the interior of the apparatus 100 by the controller 160 is provided intensely only to the distal end (i.e., the first current providing part 152) of the hollow tube 120 in an uninsulated state. Accordingly, the first current may react with the gas that flows through the hollow tube 120 at the distal end of the hollow tube 120 and may output plasma to the outside of the apparatus 100.

Then, the second current may be an RF current, but the present disclosure is not limited thereto.

The outer surface of the housing 110, except for the second current providing part 154, may be formed in an insulated state. This may be for alleviating the pain of the patient by minimizing an area that directly provides a current to the skin while the remaining parts, except for a part that outputs a current, is in an insulated state.

The controller 160 may control the first current providing part 152 and the second current providing part 154 to sequentially provide the first current and the second current.

More specifically, the controller 160 may sequentially provide the plasma and the second current to the skin through switching of a first mode for providing the first current and a second mode for providing the second current.

For this switching of the modes, the stimulation providing apparatus 100 may be connected to a first electrode (not illustrated) and a second electrode (not illustrated). More specifically, the first current providing part 152 may be connected to the first electrode for activating the first mode, and the second current providing part 154 may be connected to the second electrode for activating the second mode.

Then, the locations of the first electrode and the second electrode may be changed. That is, the controller 160 may set their locations so that a distance between the first electrode and the second electrode is within a range, by which they do not influence each other. Specifically, the stimulation providing apparatus 100 may further include an electrode moving part (not illustrated) for moving the first electrode and the second electrode, and in this case, the controller 160 may control movement of the first electrode and movement of the second electrode through the electrode moving part or adjust an interval between the first and second electrodes.

The locational movement of the first electrode and the second electrode may be performed not only by the electrode moving part but also by an external apparatus depending on the embodiment.

According to an embodiment, in the first mode, the controller 160 may apply a voltage only to the first electrode so that the first current is provided only through the first current providing part 152 connected to the first electrode. In the second mode, the controller 160 may apply a voltage only to the second electrode so that the second current is provided only through the second current providing part 154 connected to the second electrode.

According to an embodiment, in the first mode, the controller 160 applies a voltage of a first intensity through the first electrode to provide the first current through the first current providing part 152, and in the second mode, the controller 160 may apply a voltage of a second intensity through the second electrode to provide the second current through the second current providing part 154. That is, the controller 160 may vary the intensity of the power provided to the stimulation providing apparatus 100 depending on the mode. Specifically, the first current is for outputting the plasma provided to the skin for treatment, and the second current is provided directly to the skin for treatment so that the intensities of the powers applied when the modes are activated may be different.

The controller 160 in the present disclosure may not be included in the interior of the housing 110, but may be included in an individual apparatus outside the housing 110 to control the components included in the interior of the housing 110.

According to an embodiment, the controller 160 may be included in a handpiece (not illustrated) that is connected to the housing 110.

In more detail, the housing 110 that is formed of a needle type or a cannula type may be connected to the handpiece (not illustrated) through at least one connection member.

The handpiece (not illustrated) is a part which the doctor grips, and the housing 110 formed of a needle type or a cannula type may be inserted into the skin such that the first current and the plasma are controlled to be sequentially output by the controller 160 included in the handpiece (not illustrated) while the doctor moves the handpiece (not illustrated) on the skin of the patient.

The controller 160 may control the gas to be injected through the injection hole 130 when it is sensed that the housing 110 is inserted into the skin at a preset depth or more.

The controller 160 may control the first current providing part 152 and the second current providing part 154 to provide a current when it is sensed that the housing 110 is inserted into the skin at the preset depth or more. That is, when the housing 110 is inserted into the skin at the preset depth or more (for example, a depth that is large enough to reach the dermal layer), the controller 160 may perform a control to provide a current to the first current providing part 152 and the second current providing part 154.

As described above, the stimulation providing apparatus 100 of the present disclosure may be formed of a needle type or cannula type.

According to an embodiment, a needle tip that provides the RF current and the plasma-based stimulation may be implemented by using the stimulation providing apparatus 100 formed of a needle type. That is, the stimulation providing apparatus 100 formed of a needle type may be included in the needle tip as a needle unit. Hereinafter, the needle tip that provides an RF current and plasma-based stimulus will be described.

The needle tip may include a needle fixing part and a plurality of needles that are inserted into the skin.

A plurality of needles may be inserted into and fixed to the needle fixing part.

Each of the needles includes the hollow tube that is formed along a lengthwise direction of the housing in an interior of the housing, the injection hole that is formed at one end of the hollow tube, and into which at least one gas is injected, the first current providing part that is formed at a distal end of an inner surface of the hollow tube, and that provides a first current to an interior of the hollow tube, the second current providing part that is formed at a distal end of an outer surface of the housing, and that provides a second current to the skin, the controller that controls the first current providing part and the second current providing part such that the first current and the second current are sequentially provided, and the at least one discharge hole that is formed at an opposite end of the hollow tube, and that discharges plasma generated at a distal end of the hollow tube. Here, a detailed description of the hollow tube 120, the injection hole 130, the discharge hole 140, the first current providing part 152, the second current providing part 154, and the controller 160 are the same as those described with reference to FIGS. 7 and 8, and will be omitted.

According to an embodiment, a cannula tip that provides an RF current and plasma-based stimulus may be implemented by using the stimulation providing apparatus 100 formed of a cannula type. That is, the stimulation providing apparatus 100 formed of a cannula type may be included in the cannula tip as a cannula unit. Hereinafter, the cannula tip that provides an RF current and plasma-based stimulus will be described.

The cannula tip may include a cannula fixing part and a plurality of cannulas that are inserted into the skin.

A plurality of cannulas may be inserted into and fixed to the cannula fixing part.

Each of the cannulas includes the hollow tube that is formed along a lengthwise direction of the housing in an interior of the housing, the injection hole that is formed at one end of the hollow tube, and into which at least one gas is injected, the first current providing part that is formed at a distal end of an inner surface of the hollow tube, and that provides a first current to an interior of the hollow tube, the second current providing part that is formed at a distal end of an outer surface of the housing, and that provides a second current to the skin, the controller that controls the first current providing part and the second current providing part such that the first current and the second current are sequentially provided, and the at least one discharge hole that is formed at an opposite end of the hollow tube, and that discharges plasma generated at a distal end of the hollow tube. Here, a detailed description of the hollow tube 120, the injection hole 130, the discharge hole 140, the first current providing part 152, the second current providing part 154, and the controller 160 are the same as those described with reference to FIGS. 7 and 8, and will be omitted.

The operations of the method or algorithm described in relation to the embodiments of the present disclosure may be implemented directly by hardware, a software module executed by hardware, or a combination thereof. The software module may reside in a random access memory (RAM), a read only memory (ROM), an erasable programmable ROM (EPROM), an electrically erasable programmable ROM (EEPROM), a flash memory, a hard disk, a detachable disk, or a CD-ROM, or in a computer readable storage medium of an arbitrary form that is well known in the field, to which the present disclosure pertains.

According to the present disclosure, because a current is provided to an interior of the apparatus, and the outer surface of the apparatus of the needle or cannula type inserted into the skin is formed in an insulated state, the current may not be provided to an area inside the skin, in which the apparatus is inserted. This may alleviate the pain that is felt by a patient during skin care or treatment.

In addition, by sequentially providing the RF current and the plasma, it is possible to obtain both an effect of regenerating skin tissues with the RF current and an effect of regenerating skin tissues with the plasma.

The effects of the present disclosure are not limited to the aforementioned ones, and any other effects not mentioned herein will be clearly understood from the following description by those skilled in the art to which the present disclosure pertains.

Until now, the embodiments of the present disclosure have been described with reference to the accompanying drawings, but it may be understood that an ordinary person in the art, to which the present disclosure pertains, may carry out the present disclosure in another specific form while not changing the technical spirit or the essential features. Therefore, it should be understood that the embodiments described above are all illustrative, and not restrictive.

What is claimed is:

1. An apparatus for providing a stimulation based on an RF current and plasma, comprising:

a housing inserted into skin;

a hollow tube formed along a lengthwise direction of the housing in an interior of the housing;

an injection hole formed at one end of the hollow tube, and into which at least one gas is injected;

a first current providing part formed at a distal end of an inner surface of the hollow tube, and configured to provide a first current to an interior of the hollow tube;

a second current providing part formed at a distal end of an outer surface of the housing, and configured to provide a second current to the skin;

a controller configured to control the first current providing part and the second current providing part such that the first current and the second current are sequentially provided; and a plurality of discharge holes, which are formed at an opposite end of the hollow tube, and configured to discharge plasma generated at a distal end of the hollow tube, wherein the plurality of discharge holes are configured to be in a first pattern status, in which first discharge holes among the plurality of discharge holes are opened such that the plasma is discharged only from the first discharge holes, and the plurality of discharge holes are configured to be in a second pattern status, in which second discharge holes among the plurality of discharge holes are opened such that the plasma is discharged only from the second discharge holes, and wherein the first discharge holes are arranged in a shape of a first pattern, and the second discharge holes are arranged in a shape of a second pattern, which is different from the first shape.

2. The apparatus of claim 1, wherein the controller sequentially control the first current providing part and the second current providing part, such that the plasma is provided to the skin through switching of a first mode for providing the first current and a second mode for providing the second current.

3. The apparatus of claim 2, wherein the first current providing part is connected to a first electrode for activating the first mode, and the second current providing part is connected to a second electrode for activating the second mode.

4. The apparatus of claim 3, wherein in the first mode, the controller provides the first current through the first current providing part by applying a voltage of a first intensity through the first electrode, and wherein in the second mode, the controller provides the second current through the second current providing part by applying a voltage of a second intensity through the second electrode.

5. The apparatus of claim 1, wherein a portion of the inner surface of the hollow tube, except for the first current providing part, is formed in an insulated state, and wherein a portion of the outer surface of the housing, except for the second current providing part, is formed in an insulated state.

6. The apparatus of claim 1, wherein when sensing that the housing is inserted into the skin by a preset depth or more, the controller controls the first current providing part to provide the first current or controls the second current providing part to provide the second current.

7. The apparatus of claim 1, wherein the housing is formed of a needle type or a cannula type.

8. An apparatus for providing a stimulation based on plasma, comprising:

a housing inserted into skin;

a hollow tube formed along a lengthwise direction of the housing in an interior of the housing;

an injection hole formed at one end of the hollow tube, and into which at least one gas is injected;

a current providing part formed at a distal end of the hollow tube, and configured to provide a current to an interior of the hollow tube;

a controller configured to control the current providing part to apply the current to a gas flowing through the hollow tube, such that plasma is generated at the distal end of the hollow tube; and a plurality of discharge holes, which are formed at an opposite end of the hollow tube, and through which the plasma generated at the distal end of the hollow tube is discharged, wherein the plurality of discharge holes are configured to be in a first pattern status, in which first discharge holes among the plurality of discharge holes are opened such that the plasma is discharged only from the first discharge holes, and the plurality of discharge holes are configured to be in a second pattern status, in which second discharge holes among the plurality of discharge holes are opened such that the plasma is discharged only from the second discharge holes, and wherein the first discharge holes are arranged in a shape of a first pattern, and the second discharge holes are arranged in a shape of a second pattern, which is different from the first shape.

9. The apparatus of claim 8, wherein an outer surface of the housing is formed in an insulated state.

10. The apparatus of claim 8, wherein when sensing that the housing is inserted into the skin by a preset depth or more, the controller controls the current providing part to provide the current.

11. The apparatus of claim 8, wherein an inner surface of the housing is an outer surface of the hollow tube.

12. The apparatus of claim 8, wherein the housing is formed of a needle type.

13. The apparatus of claim 8, wherein the housing is formed of a cannula type.

14. A needle tip for providing a stimulation based on plasma, the needle tip comprising:

a needle fixing part; and a plurality of needles inserted into skin, wherein each of the plurality of needles includes:

a hollow tube formed along a lengthwise direction of the needle at a center of an interior thereof;

an injection hole formed at one end of the hollow tube, and to which at least one gas is injected;

a current providing part formed at a distal end of the hollow tube, and configured to provide a current to an interior of the hollow tube;

a controller configured to generate plasma at the distal end of the hollow tube by controlling the current providing part to apply the current to a gas flowing through the hollow tube; and a plurality of discharge holes, which are formed at an opposite end of the hollow tube, and through which the plasma generated at the distal end of the hollow tube is discharged, wherein the plurality of discharge holes are configured to be in a first pattern status, in which first discharge holes among the plurality of discharge holes are opened such that the plasma is discharged only from the first discharge holes, and the plurality of discharge holes are configured to be in a second pattern status, in which second discharge holes among the plurality of discharge holes are opened such that the plasma is discharged only from the second discharge holes, and wherein the first discharge holes are arranged in a shape of a first pattern, and the second discharge holes are arranged in a shape of a second pattern, which is different from the first shape.

* * * * *